US010357432B2

(12) United States Patent
Dollinger

(10) Patent No.: US 10,357,432 B2
(45) Date of Patent: Jul. 23, 2019

(54) DEVICE FOR COATING PARTICULATE MATERIAL

(71) Applicant: PHARMA TECHNOLOGY S.A., Nivelles (BE)

(72) Inventor: Martial Dollinger, Braine l'Alleud (BE)

(73) Assignee: PHARMA TECHNOLOGY S.A., Thines (Nivelles) (BE)

( * ) Notice: Subject to any disclaimer, the term of this patent is extended or adjusted under 35 U.S.C. 154(b) by 0 days.

(21) Appl. No.: 15/559,010

(22) PCT Filed: Mar. 19, 2015

(86) PCT No.: PCT/EP2015/000601
§ 371 (c)(1),
(2) Date: Sep. 15, 2017

(87) PCT Pub. No.: WO2016/146141
PCT Pub. Date: Sep. 22, 2016

(65) Prior Publication Data
US 2018/0078458 A1    Mar. 22, 2018

(51) Int. Cl.
*B05B 13/02* (2006.01)
*B05C 19/00* (2006.01)
(Continued)

(52) U.S. Cl.
CPC ............ *A61J 3/005* (2013.01); *A61K 9/2893* (2013.01); *B01J 2/006* (2013.01); *B01J 2/18* (2013.01);
(Continued)

(58) Field of Classification Search
CPC ................................... A61J 3/005
See application file for complete search history.

(56) References Cited

U.S. PATENT DOCUMENTS

| 366,820 | A | | 7/1887 | Donner | |
|---|---|---|---|---|---|
| 2,983,051 | A | * | 5/1961 | Zimmermann | F28C 3/14 34/164 |

(Continued)

FOREIGN PATENT DOCUMENTS

| FR | 2258895 A1 | 8/1975 |
|---|---|---|
| FR | 2311583 A2 | 12/1976 |
| WO | 95/19838 A1 | 7/1995 |

OTHER PUBLICATIONS

International Search Report dated Jan. 12, 2016, issued in corresponding International Application No. PCT/EP2015/000601, filed Mar. 19, 2015, 3 pages.
(Continued)

*Primary Examiner* — Binu Thomas
(74) *Attorney, Agent, or Firm* — Christensen O'Conner Johnson Kindness PLLC

(57) ABSTRACT

A particulate material coating device, comprising a vertical central column, a supply conduit for supplying the device with particulate material to be coated and a discharge conduit for discharging coated particulate material, a conveying ramp connected to the central column and a plurality of sprayers for spraying a coating agent. The supply means is arranged at the top of the device and the discharge conduit is arranged at the base of the device. The conveying ramp comprises a plurality of ramp sections arranged one above the other so as to define, between two successive sections, a drop zone for the particulate material to fall between each of the successive sections. The device aims to ensure that the particulate material is transported without areas of accumulation as well as a homogeneous coating.

12 Claims, 3 Drawing Sheets

(51) Int. Cl.
   *B65G 27/32* (2006.01)
   *A61J 3/00* (2006.01)
   *F26B 17/26* (2006.01)
   *A61K 9/28* (2006.01)
   *B01J 2/00* (2006.01)
   *B01J 2/18* (2006.01)
   *A23G 3/34* (2006.01)
   *B65G 27/02* (2006.01)

(52) U.S. Cl.
   CPC ........ *B05B 13/025* (2013.01); *B05B 13/0278* (2013.01); *B65G 27/32* (2013.01); *F26B 17/266* (2013.01); *A23G 3/0089* (2013.01); *B05C 19/00* (2013.01); *B65G 27/02* (2013.01)

(56) References Cited

U.S. PATENT DOCUMENTS

| | | | | |
|---|---|---|---|---|
| 3,292,775 A * | 12/1966 | White | ............... | B65G 49/0427 198/771 |
| 3,343,812 A * | 9/1967 | Moulton | ............... | B01F 11/006 198/562 |
| 4,035,151 A | 7/1977 | Czerny et al. | | |
| 4,237,622 A * | 12/1980 | Francis | ............... | F26B 3/04 34/147 |
| 5,067,431 A * | 11/1991 | Heitmiller | ............... | B65G 49/0427 118/423 |
| 5,567,238 A * | 10/1996 | Long, Jr. | ............... | A01C 1/06 118/13 |
| 7,810,446 B2 * | 10/2010 | Degady | ............... | A23G 3/0089 118/13 |
| 2008/0257689 A1* | 10/2008 | Romer | ............... | B65G 27/04 198/657 |
| 2010/0092694 A1* | 4/2010 | Bohlmann | ............... | A61J 3/005 118/642 |
| 2012/0189748 A1 | 7/2012 | Corrigan | | |

OTHER PUBLICATIONS

Written Opinion of the International Searching Authority dated Jan. 12, 2016, issued in corresponding International Application No. PCT/EP2015/000601, filed Mar. 19, 2015, 5 pages.

* cited by examiner

DEVICE FOR COATING PARTICULATE MATERIAL

CROSS-REFERENCE TO RELATED APPLICATION

This application is the National Stage of International Application No. PCT/EP2015/000601, filed Mar. 19, 2015, the disclosure of which is hereby incorporated by reference in its entirety.

FIELD OF THE DISCLOSURE

Embodiments of the present disclosure relate to a device for coating particulate material, in particular pharmaceutical tablets

BACKGROUND

Such devices are used for applying, to a particulate material, a surface layer of a coating agent intended to protect the enrobed particles from any external contaminants or to preserve their physical integrity. The coating agent may contain a dye and/or a substance conferring improved hardness and/or smoothing on the enrobed particles and a substance deferring in time the release of the active principle of a drug tablet. When such coating devices are used in the pharmaceutical industry for coating drug tablets, a coating device is generally disposed in a region situated between a region where a device is situated for de-dusting tablets after manufacture thereof from compressed drug powder and a region where a device is situated for packaging the coated tablets in suitable packaging.

Various types of device for coating particulate material and in particular pharmaceutical tablets exist according to the prior art: thus the patent application US 2010/0092694 A1 relates to a device for coating pharmaceutical tablets comprising a vertical chamber in which there is arranged a cylindrical tower comprising a central column to which there is fixed a continuous helical ramp for transporting the tablets to be coated from the base of the tower where they are introduced into the device as far as the top layer of where they are discharged after coating. The ascending movement of the tablets in the tower is obtained by vibration of the latter. During their rise along the ramp of the tower, the tablets are coated with coating agent sprayed by spray means oriented towards said ramp.

Such a device has the drawback that, since the particulate material to be coated is moved in the device in an ascending manner while the coating agent is sprayed thereon, the wetting of the material by the coating agent slows it in its rise since the wetted particles "skate" on the ramp of the tower, which causes localised conglomerations of this particulate material, such conglomerations being unfavourable to optimum coating since, in these conglomeration regions, the particulate material receives too much coating agent and the coated particles stick to one another there. Moreover, in a device according to the patent application in question, the particles to be coated have a tendency not to be exposed to the coating agent uniformly over their entire surface since they tend to keep their initial orientation during their rise.

The patent application US 366 820 solves this problem by proposing a device for spraying water onto rocky particles in order to wash these particles, in which they move by gravity on inclined flat tables disposed one above the other and are exposed to the spray when they fall from one table to the one underlying it.

Such a device has the drawback of being very bulky. This is because the particles move thereon by gravity and consequently it is necessary for the inclined tables that it comprises to be sufficiently inclined to ensure the movement in question, which gives rise to a significant height of the device for a given number of spray zones. Moreover, the device in question has a complex structure. This is because a frame peripheral to the device must be provided so that each of the aforementioned tables is fixed thereto.

WO 95/19838 responds to the aforementioned problem of conglomeration by proposing a device for coating particles with fertilising agent in which particles move by gravity on slightly inclined flat tables disposed one under the other and are coated with fertilising agent as they fall from one table to the one underlying it, by spray means disposed perpendicularly to the drop zone of said particles. To ensure correct movement of the particles while the tables that it comprises are slightly inclined, the device described requires that a means for fluidising said particles be provided, consisting of air injectors disposed under each table in order to project air through orifices arranged in these tables so as to fluidise thereon the particles in question so that they end up correctly in the drop zone in which they are coated with fertilising agent. The device in question therefore has the drawback of requiring a structure that is even more complex than the one of the device according to US 366 820.

SUMMARY

Embodiments of the present disclosure aim to overcome the aforementioned drawbacks by proposing a device for coating particulate material, comprising a central column arranged so as to be disposed vertically, a supply means for supplying the device with particulate material to be coated and a discharge means for discharging coated particulate material, the device comprising a conveying ramp connected to the central column and a plurality of spray means for spraying a coating agent, each spray means being arranged so as to orient said spray towards said particulate material while it is conveyed in the device. The supply means is arranged at the top of the device and the discharge means is arranged at the base of the device and the conveying ramp comprises a plurality of ramp sections arranged one above the other so as to define, between two successive sections, a drop zone for said particulate material to fall between each of said successive sections.

Because the supply means of the device is arranged at the top thereof, because its discharge means is arranged at its base and because the conveying of comprises a plurality of ramp sections arranged one above the other so as to define, between two successive sections, a drop zone for the particulate material between each of said successive sections, the particles are transported in the device without areas of accumulation of these particles appearing therein, since, even if wetted by the coating agent, the particles of material transported in the device do not "skate" on its ramp since they are assisted in their descent thereon by gravity. Moreover, the orientation of these particles is modified through the drop zones of this ramp, which enables them to be exposed over their entire surface to the spraying and consequently to obtain uniform coating of said particles.

DESCRIPTION OF THE DRAWINGS

The foregoing aspects and many of the attendant advantages of the claimed subject matter will become more readily appreciated as the same become better understood by reference to the following detailed description, when taken in conjunction with the accompanying drawings, wherein:

DETAILED DESCRIPTION

Figure 1:
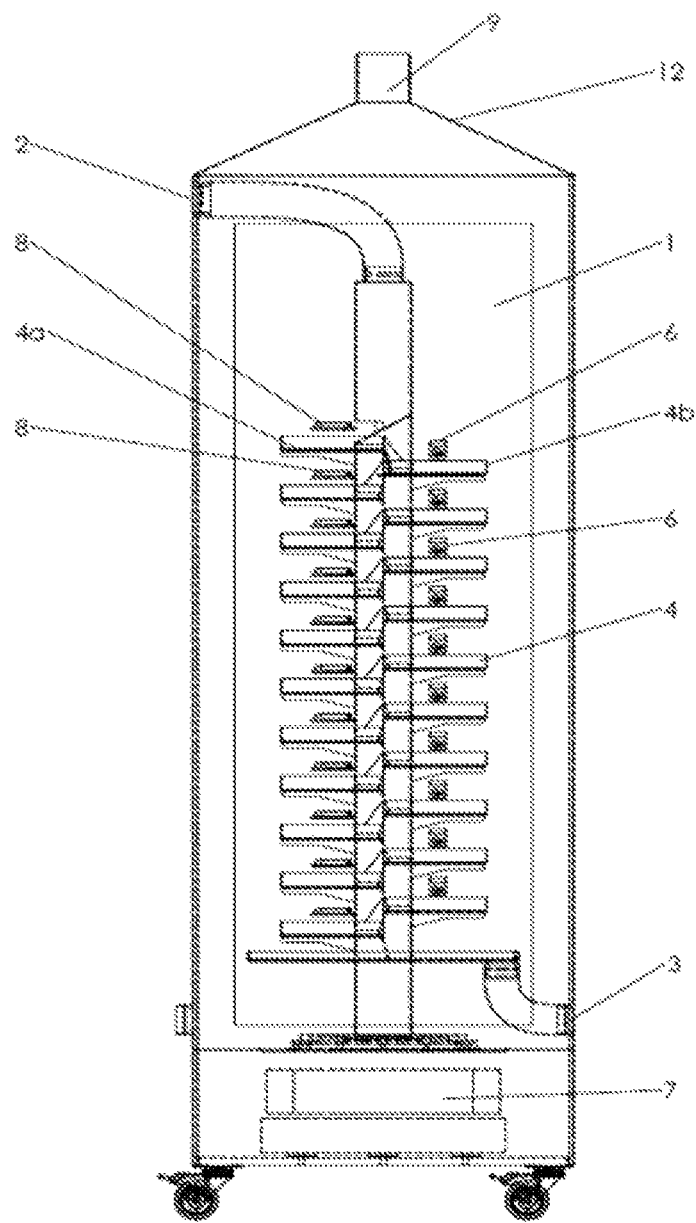
FIG. 1 is a front view of an embodiment.
Figure 2:
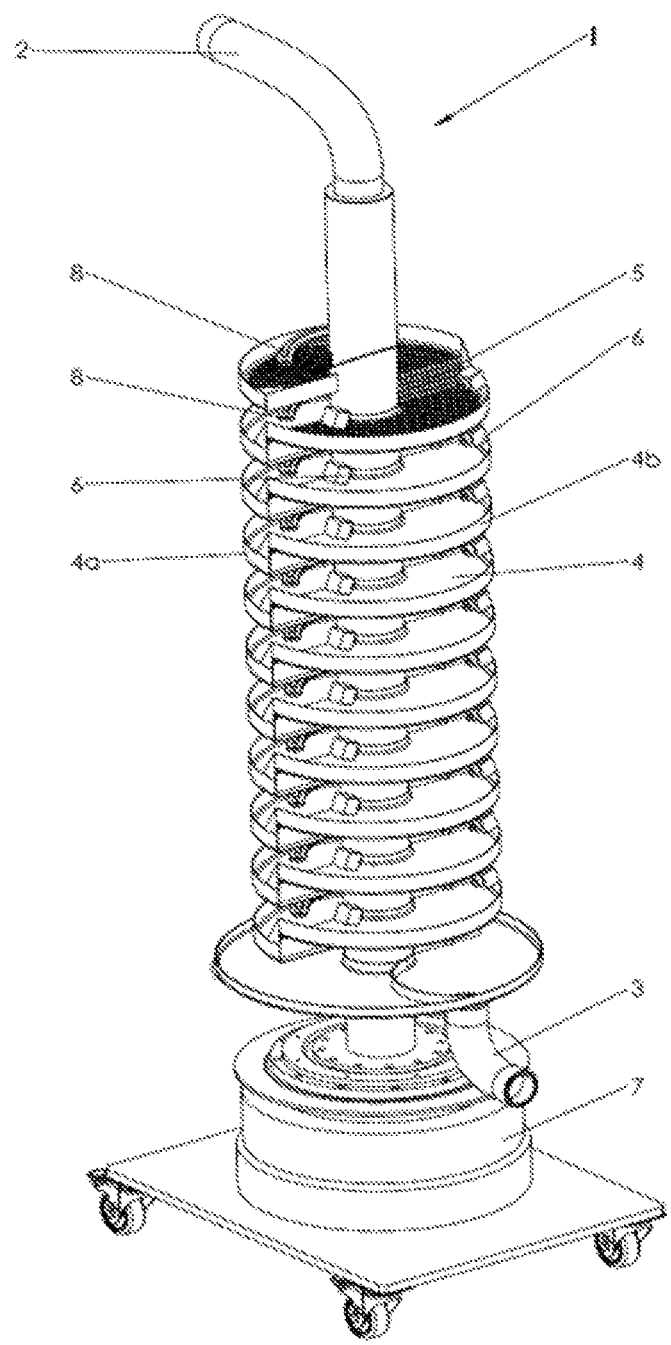
FIG. 2 is a perspective view of the embodiment illustrated in FIG. 1, without its confinement chamber.
Figure 3:
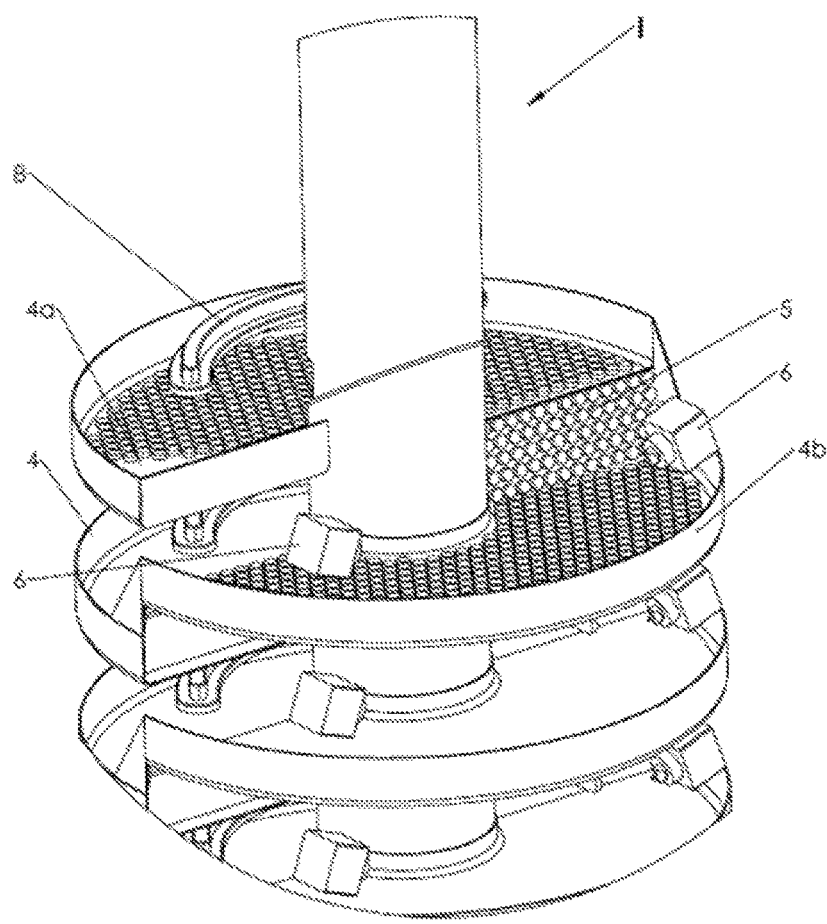
FIG. 3 is an enlargement of the top part of the view in FIG. 2.

The detailed description set forth below in connection with the appended drawings, where like numerals reference like elements, is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the claimed subject matter to the precise forms disclosed.

Referring to the FIGURES, a device I for coating particulate material is illustrated therein, comprising a central column 1 arranged to be disposed vertically, a supply means 2 for supplying the device with particulate material to be coated and a discharge means 3 for discharging the coated particulate material, the device comprising a conveying ramp 4 connected to the central column and a plurality of spray means 6 for spraying a coating agent, each spray means being arranged to orient said spraying towards said particulate material as it is conveyed in the device.

The supply means is arranged at the top of the device and the discharge means at its base so that the particulate material is conveyed in this device without any areas of accumulation of this material being created therein, because of the effect of gravity thereon.

The conveying ramp comprises a plurality of ramp sections 4a, 4b arranged one above the other so as to define, between two successive sections, a drop zone 5 for said particulate material between each of said successive sections. Two successive sections can be connected together as in the embodiment illustrated by connection elements. Alternatively, in an embodiment that is not illustrated, a section higher than the successive lower section may slightly overlap the latter so that the particles of particulate material transported in the device all fall correctly from the top section onto the lower section.

The device also comprises a means 7 arranged to impart an oscillating or vibratory movement to the ramp in order to convey the particulate material between the supply means and the discharge means of the device. In the embodiment illustrated, this means consists of an oscillating motor arranged under the central column and connected to the latter so as to be able to impart the desired oscillating or vibratory movement entirely to it and so as also to impart the same movement to the ramp of the device connected to this central column. In this way, the tablets are driven from the supply means to the discharge means of the device by virtue of this movement in addition to the effect of gravity, and this by a single means, which confers on said device a simple and practical structure.

In the embodiment illustrated, each ramp section is planar and arranged orthogonally to the central column so as to be disposed horizontally when the column is vertical. This configuration makes it possible to obtain a very compact device because of the small height occupied by two successive ramp sections. Alternatively, ramp sections oblique with respect to the central column may be used, which makes it possible to increase the speed of conveying of particulate material in the device by subjecting it further to the effect of driving by gravity between the top and base of said device.

In the embodiment illustrated, the ramp sections have an outer edge in an arc of a circle, which enables the particulate material that is conveyed thereon to be conveyed at the same angular speed over the entire radius of such ramp sections, which promotes optimum distribution of said material over each ramp section and prevents areas where particulate material accumulates forming therein because of different angular speeds of these particles. When the ramp sections are not orthogonal but oblique with respect to the central column of the device, they may nevertheless fit in a cylinder and in this way keep the aforementioned advantage in terms of constant angular speed, in particular when these ramp sections have a helical cross section form.

The device also comprises a plurality of drying means 8 for drying the coated particulate material, formed in the embodiment illustrated by infrared radiant lamps, each such lamp being oriented in the direction of a different ramp section so that the coating of the particulate material that is conveyed thereon is dried during the transit of this coated particulate material over said ramp section. Any other drying means known to persons skilled in the art could alternatively be used in the context of the disclosure. In practice, as illustrated in the FIGURES, the spraying and drying means are disposed in alternation above successive ramp sections, a spraying means overhanging a first ramp section and a drying means overhanging the second ramp section that underlies the first section.

The device also comprises a confinement chamber 10 arranged to isolate the elements constituting the device from outside same so that the sprayed coating agent does not escape therefrom and so that the coating is not interfered with by ambient air currents, as well as a means 9 for renewing the air contained in the device, so that this air does not become excessively moist because of the spraying in the coating agent device. This means may for example consist of a fan disposed under or above the ramp of the device and blowing air through it.

In practice, the device illustrated is used for the coating of particulate material consisting of pharmaceutical tablets but may also serve to coat other particulate materials.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

The invention claimed is:

1. A device for coating particulate material, comprising:
a central column arranged so as to be disposed vertically;
supply means for supplying the device with particulate material to be coated;
discharge means for discharging coated particulate material;
a conveying ramp connected to the central column; and a plurality of spray means for spraying a coating agent, each spray means being arranged so as to orient said spray towards said particulate material while it is conveyed in the device, wherein said particulate material consists of pharmaceutical tablets, wherein said supply means is arranged at the top of the device and said discharge means is arranged at a base of said device and wherein said conveying ramp comprises a plurality of ramp sections arranged one above the other so as to define, between two successive sections, a drop zone for said particulate material to fall between each of said successive sections, wherein said device further comprises a plurality of drying means for drying coated particulate material, and wherein said plurality of spray means and said plurality of drying means are disposed in an alternating way above said plurality of ramp sections, one spray means of said plurality of spray means overhanging a first ramp section of said two successive ramp sections and one drying means of said plurality of said drying means overhanging a second ramp section of said two successive ramp sections that is positioned below said first ramp section.

2. The device according to claim 1, comprising a means arranged to impart an oscillating or vibratory movement to the conveying ramp in order to convey the particulate material between the supply means and the discharge means of the device.

3. The device according to claim 2, wherein each ramp section is planar and arranged orthogonally to the central column.

4. The device according to claim 3, wherein each ramp section has an outer edge in an arc of a circle.

5. The device according to claim 1, comprising means for renewing air contained in the device.

6. The device according to claim 1, wherein each ramp section is planar, arranged orthogonally to the central column, and has an outer edge in a shape of a semicircle.

7. The device according to claim 1, wherein each spray means of said plurality of spray means is configured so as to direct said spray towards a drop zone between two successive ramp sections.

8. A device for coating particulate material, comprising:

a central column arranged so as to be disposed vertically;

a supply opening configured to supply the device with particulate material to be coated;

a discharge opening configured to discharge coated particulate material;

a conveying ramp connected to the central column; and a plurality of sprayers configured to spray a coating agent, each sprayer being arranged so as to orient said spray towards said particulate material while it is conveyed in the device, wherein said particulate material consists of pharmaceutical tablets, wherein said supply opening is arranged at the top of the device and the discharge opening is arranged at a base of said device and wherein said conveying ramp comprises a plurality of ramp sections arranged one above the other so as to define, between two successive sections, a drop zone for said particulate material to fall between each of said successive sections, wherein said device further comprises a plurality of heat sources configured to dry coated particulate material, and wherein said plurality of sprayers and said plurality of heat sources are disposed in an alternating way above said plurality of ramp sections, one sprayer of said plurality of sprayers overhanging a first ramp section of said two successive ramp sections and one heat sources of said plurality of heat sources overhanging a second ramp section of said two successive ramp sections that is positioned below said first ramp section.

9. The device according to claim 8, further comprising a motor arranged to impart an oscillating or vibratory movement to the conveying ramp in order to convey the particulate material between the supply opening and the discharge opening of the device.

10. The device according to claim 8, wherein at least one heat source of said plurality of heat sources is associated with each sprayer of said plurality of sprayers, the at least one heat source configured to assist drying of the coating agent sprayed by the associated sprayer.

11. The device according to claim 8, further comprising a fan configured to renew air contained in the device.

12. The device according to claim 8, further comprising a blower configured to renew air contained in the device.

* * * * *